(12) United States Patent
Zhou et al.

(10) Patent No.: US 12,239,324 B2
(45) Date of Patent: Mar. 4, 2025

(54) MEDICAL INSTRUMENT

(71) Applicant: SHANGHAI MICROPORT CARDIOADVENT CO., LTD., Shanghai (CN)

(72) Inventors: Yi Zhou, Shanghai (CN); Tianyu Liu, Shanghai (CN); Zexun Zhu, Shanghai (CN); Yao Yao, Shanghai (CN); Junfei Li, Shanghai (CN)

(73) Assignee: SHANGHAI MICROPORT CARDIOADVENT CO., LTD., Shanghai (CN)

( * ) Notice: Subject to any disclaimer, the term of this patent is extended or adjusted under 35 U.S.C. 154(b) by 412 days.

(21) Appl. No.: 17/772,320

(22) PCT Filed: Oct. 20, 2020

(86) PCT No.: PCT/CN2020/122019
§ 371 (c)(1),
(2) Date: Apr. 27, 2022

(87) PCT Pub. No.: WO2021/082974
PCT Pub. Date: May 6, 2021

(65) Prior Publication Data
US 2022/0401112 A1    Dec. 22, 2022

(30) Foreign Application Priority Data

Oct. 28, 2019   (CN) .......................... 201911032196.1

(51) Int. Cl.
*A61B 17/12*    (2006.01)
*A61F 2/24*     (2006.01)

(52) U.S. Cl.
CPC .......... *A61B 17/12172* (2013.01); *A61F 2/24* (2013.01); *A61B 2017/12054* (2013.01)

(58) Field of Classification Search
CPC .... A61B 17/12172; A61B 2017/12054; A61B 17/12122; A61B 17/12031;
(Continued)

(56) References Cited

U.S. PATENT DOCUMENTS

2006/0020319 A1    1/2006   Kim et al.
2009/0216263 A1*   8/2009   Tekulve ........... A61B 17/12022
                                                          606/200
(Continued)

FOREIGN PATENT DOCUMENTS

CN    101415379 A    4/2009
CN    102917669 A    2/2013
(Continued)

*Primary Examiner* — Shaun L David
*Assistant Examiner* — Rachael L Geiger
(74) *Attorney, Agent, or Firm* — MUNCY, GEISSLER, OLDS & LOWE, P.C.

(57) ABSTRACT

A medical instrument (1000) includes a stent (100) and a constraining structure (300). The constraining structure (300) constrains, and thereby prevents tangling of, a trailing section of the stent (100), ensuring successful release of the stent (100). Specifically, the stent (100) has a first proximal end and an opposing first distal end. The first distal end is configured with an expanded configuration and a collapsed configuration. The trailing section at the first distal end includes a number of protrusions (111). The constraining structure (300) includes a body (310) and a clamping mechanism (320). The clamping mechanism (320) is disposed at a distal end of the body (310), and the body (310) extends from the first proximal end to the first distal end. The clamping mechanism (320) limits relative movement and thus prevents tangling of the protrusions (111) by passing through all or some of the protrusions (111). Additionally, it allows the stent (100) to be less deformed within a delivery sheath and thereby enables it to successfully expand when pushed out of the sheath.

12 Claims, 7 Drawing Sheets

(58) Field of Classification Search
CPC .......... A61B 17/12168; A61B 17/0057; A61B 2017/00575; A61B 17/12022; A61F 2/24
See application file for complete search history.

(56) References Cited

U.S. PATENT DOCUMENTS

| | | | |
|---|---|---|---|
| 2010/0121434 A1* | 5/2010 | Paul | A61F 2/2418 623/2.11 |
| 2011/0054515 A1 | 3/2011 | Bridgeman et al. | |
| 2011/0178588 A1* | 7/2011 | Haselby | A61F 2/9661 623/1.11 |
| 2011/0301702 A1* | 12/2011 | Rust | A61F 2/2418 623/2.11 |
| 2016/0302950 A1 | 10/2016 | Marmur et al. | |
| 2017/0266003 A1* | 9/2017 | Hammer | A61F 2/2436 |
| 2018/0110622 A1 | 4/2018 | Gregg et al. | |

FOREIGN PATENT DOCUMENTS

| | | |
|---|---|---|
| CN | 104688292 A | 6/2015 |
| CN | 106037852 A | 10/2016 |
| CN | 108236479 A | 7/2018 |
| EP | 3085310 A1 | 10/2016 |

* cited by examiner

MEDICAL INSTRUMENT

TECHNICAL FIELD

The present invention relates to the technical field of medical instruments and, more specifically, to a medical instrument.

BACKGROUND

Atrial fibrillation (AF) is the most common perpetual arrhythmia seen in clinical practice and is associated with a risk of causing ischemic stroke. Therefore, the prevention of atrial fibrillation is of great significance. Recent studies have shown that left atrial appendage (LAA) closure is an effective countermeasure to the risk of AF-caused ischemic stroke.

Existing occluders used for LAA closure can be generally divided into two categories: cage-like ones represented by Watchman devices, which are characterized by an easy-to-fabricate integral skeleton; and two-piece ones represented by LAmbre devices, which are characterized by consisting of a locator and an occluding disc connected to the locator. During use, the locator is anchored in the LAA to provide a riveting effect. LAA closure relies principally on the occluding disc that fits over the LAA orifice, although the locator also makes a certain contribution to the occlusion. Both these types of occluders suffer from the drawback that, once they are decoupled and released, their retrieval is difficult and has to rely on the use of a snare which is, however, associated with a very low success rate.

At present, there are various semi-retrievable occluder designs featuring placement of an occluder body followed by the release of an anchor. However, these designs are prone to occluder release failure.

SUMMARY OF THE INVENTION

It is an object of the present invention to provide a medical instrument intended to resort to a constraining structure to allow a stent to be less deformed within a delivery sheath and avoid tangling of a trailing section of the stent, thereby resulting in an increased success rate in release of the stent.

In pursuit of the above object, the present invention provides a medical instrument comprising a stent having a proximal end and an opposing distal end, wherein the distal end of the stent is configured with an expanded configuration and a collapsed configuration, wherein a trailing section of the stent at the distal end comprises a plurality of protrusions, and wherein the medical instrument further comprises a constraining structure comprising a body and a clamping mechanism, the clamping mechanism disposed at the distal end of the body, the body extending from the proximal end of the stent to the distal end thereof, the clamping mechanism limiting relative movement of the protrusions by passing through all or some of them.

Optionally, the clamping mechanism may comprise a single clamping member which passes either sequentially through all the protrusions or spaced ones of the protrusions.

Optionally, the clamping mechanism may comprise at least one clamping member each passing at opposite ends through different ones of the protrusion.

Optionally, the clamping mechanism may comprise a plurality of clamping members arranged circumferentially around the stent, each of the clamping members passing at one end thereof through one of the protrusions, the clamping members passing through different protrusions.

Optionally, the number of the clamping members may be smaller than or equal to the number of the protrusions.

Optionally, the number of the protrusions may be twice the number of the clamping members.

Optionally, each clamping member may be a wire-like member made of a elastic material.

Optionally, the material of the wire-like member may be a nickel-titanium alloy or stainless steel.

Optionally, the clamping member may be shaped like the letter "C" or "V".

Optionally, each clamping member may be curved relative to the body at an angle ranging from 30° to 180°.

Optionally, the medical instrument may further comprise a proximal fixation member disposed at the proximal end of the stent and configured to bring the stent into a closed configuration at the proximal end.

Optionally, the medical instrument may further comprise a distal fixation member and a pull mechanism, the pull mechanism comprising a number of pull elements each tied, at a first end, to the distal fixation member and, at a second end, to the distal end of the stent, the distal fixation member configured to be able to move toward the proximal fixation member and thus switch the distal end of the stent from the expanded configuration to the collapsed configuration.

Optionally, the medical instrument may further comprise a biocompatible membrane which covers part of a surface of the stent, with the protrusions exposed therefrom.

Optionally, the medical instrument may further comprise a delivery device comprising a hollow push tube and a drive component, the hollow push tube detachably coupled at a distal end thereof to the proximal end of the stent, the drive component inserted through the hollow push tube into the stent and detachably coupled within the stent to the distal end thereof, the drive component configured to cause the distal end to switch from the expanded configuration to the collapsed configuration, wherein the body extends from the proximal end of the stent through the hollow push tube to the distal end of the stent.

The medical instrument of the present invention has the following advantages over the prior art:

First, during delivery, the constraining structure limits relative movement between the protrusions on the stent's trailing section, thus allowing the stent to be less deformed within the delivery sheath and avoiding tangling of the trailing section. As a result of both, it is ensured that the stent can successfully expand after it is released from the sheath, resulting in an increased success rate in release of the stent.

Second, the clamping mechanism in the constraining structure may include one or more clamping members, which can constrain the stent's trailing section in a loose and orderly manner by passing through all or some of the protrusions. This not only facilitates release of the clamping mechanism but also imparts good clamping performance thereto. Thus, better avoidance of tangling of the protrusions is achievable.

Third, constraining the trailing section of the stent with the constraining structure can avoid the sharp trailing section from damaging organ tissue before the stent is released in a desired manner.

Fourth, when the clamping mechanism includes a plurality of clamping members, the number of the clamping members is preferred to be smaller than the number of the protrusions. In this way, the protrusions can be populated by the clamping members so that there are one or more unpopulated protrusions between every two adjacent populated protrusions. This allows both a reduced size during delivery and good clamping performance.

DETAILED DESCRIPTION

Figure 1:
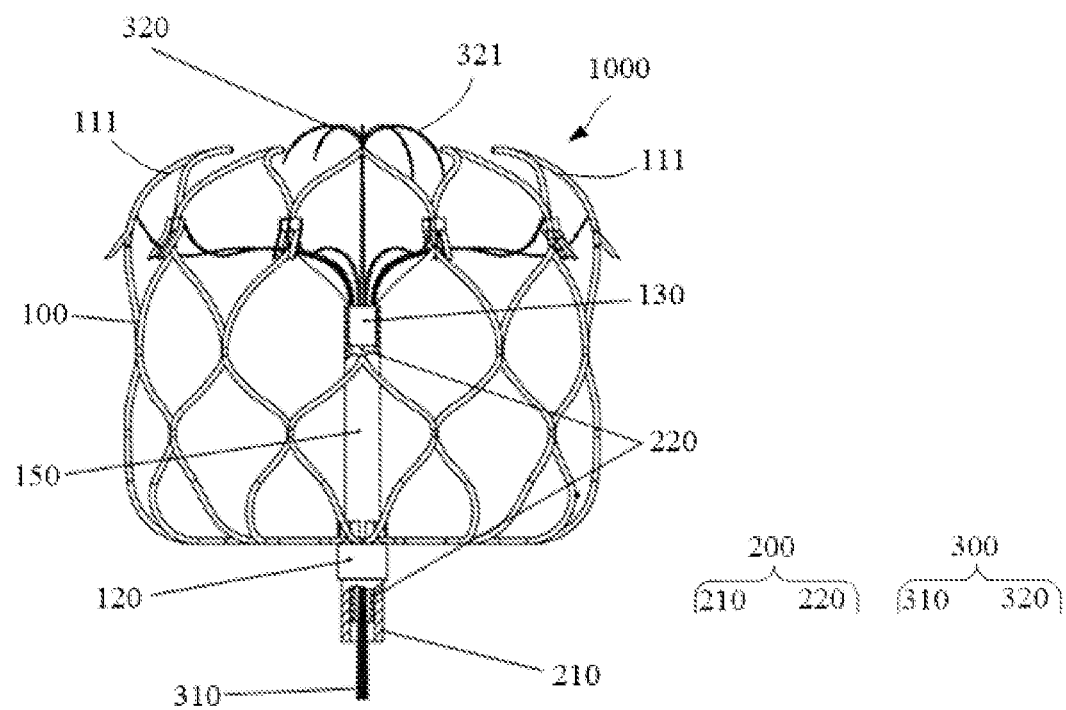
FIG. 1 is a schematic elevation view of the structure of a medical instrument according to an embodiment of the present invention.

Objects, advantages and features of the present invention will become more apparent from the following more detailed description of various embodiments thereof, which is to be read in connection with the accompanying drawings. Note that the drawings are provided in a very simplified form not necessarily drawn to exact scale for the only purpose of facilitating easy and clear description of the disclosed embodiments.

As used herein, the singular forms "a", "an" and "the" include plural referents, unless the context clearly dictates otherwise. As used herein, the term "plurality" means two or more, unless the context clearly dictates otherwise. As used herein, the term "or" is generally employed in the sense of "and/or", unless the context clearly dictates otherwise. The term "proximal end" generally refers to an end closer to an operator who operates a medical instrument, and the term "distal end" generally refers to an end farther away from the operator. Like reference numerals indicate like elements throughout the accompanying drawings.

The core concept of the present invention is to provide a medical instrument including a stent and a constraining structure configured to constrain a trailing section of the stent to avoid both excessive deformation of the stent and tangling of its trailing section during its delivery. These can facilitate successful expansion of the stent after it is released from a sheath, thereby ensuring its successful release and resulting in an increased success rate of a surgical procedure using the stent. It is added that the medical instrument of the present invention can be used to close the LAA as well as other body lumens, such as blood vessels, or as a vascular filter, a heart valve stent, a stent graft, or the like.

More specifically, the stent of the present invention has a first proximal end and an opposing first distal end. The first distal end is configured with an expanded configuration and a collapsed configuration. The trailing section at the first distal end includes a number of protrusions. The constraining structure of the present invention includes a body and clamping mechanism provided at a distal end of the body. During practical use, the body extends from the first proximal end to the first distal end, and the clamping mechanism passes through all or some of the protrusions and thus limits their relative movement. In this way, not only tangling of the trailing section is prevented during collapse of the stent, but also mutual stressing of components (e.g., a hollow push tube and a pull mechanism) involved in the delivery and release processes is avoided. Moreover, the stent is allowed to be less deformed within a delivery sheath, additionally reducing the risk of tangling of the stent's trailing section.

For example, practical use of the medical instrument of the present invention for LAA closure may involve the following processes:

Delivery: At first, the stent (i.e., a closure device) is loaded in the delivery sheath for delivery. In this process, the trailing section of the stent may be caused to collapse by manipulating both a pull mechanism of the stent itself and a drive component in a delivery device, before it can be loaded into the delivery sheath. After the stent is loaded into the delivery sheath, the constraining structure is deployed to constrain the stent's trailing section. After the intervention of the constraining structure, the drive component (e.g., a hollow pull tube or pull elements) does not need to act on the pull mechanism any longer (i.e., the trailing section of the stent is constrained by only the constraining structure, with the pull mechanism not exerting any force on the stent). As such, it is not necessary to maintain the drive component stationary relative to the hollow push tube in the delivery device, avoiding mutual stressing of the pull mechanism and the hollow push tube. This enables an operator to more easily control the shape of the stent so that the stent is less deformed within the delivery sheath, avoiding tangling of the trailing section thereof.

Release: When the stent is advanced to a target site (e.g., the LAA), it is pushed out of the delivery sheath into the LAA by manipulating the hollow push tube in the delivery device. At this point, anchoring features on the stent will not penetrate target tissue (i.e., the LAA wall) because the trailing section is still being constrained. Therefore, the operator is allowed to adjust the position of the stent by manipulating the hollow push tube. Upon the stent being tuned to a desired location, the anchoring features on the stent may be released. Responsively, these anchoring features will expand and come into engagement with the target tissue, thus anchoring the stent. During the release of the anchoring features, simply as a result of the operator gently pulling the constraining structure, the constraining structure can be removed from the stent, allowing expansion of the stent's trailing section and thus release of the anchoring features. Moreover, during release of the stent's trailing section, as this section is contained by the constraining structure in a loose and orderly manner, it will not tangle in the delivery sheath and can successfully expand after being pushed out of the sheath.

Retrieval: If it is found that the stent is not positioned as desired after the anchoring features have been released, semi-retrieval for relocation of the stent is allowed by manipulating the pull mechanism and the drive component. Specifically, the drive component may be manipulated to retract the pull mechanism so that the pull mechanism causes the stent to collapse around its first distal end. As a result, the anchoring features are removed from the target tissue, accomplishing semi-retrieval of the stent. After the stent is relocated as desired by manipulating the hollow push tube, the drive component may be again withdrawn, allowing the trailing section of the stent to expand to cause the anchoring features again penetrate the target tissue, re-anchoring the stent. In an embodiment, the aforementioned drive component may be a hollow pull tube, which is detachably (e.g., threadedly) coupled to the pull mechanism by a distal fixation member and can be manipulated to cause the pull mechanism to retract the stent at the first distal end and thus cause the stent to switch from the expanded configuration to the collapsed configuration at the first distal end. With the hollow pull tube, the stent can be retrieved once or more times, increasing the convenience of use. In another embodiment, the drive component may be a flexible pull member such as a string or wire, and preferably may be a guidewire for medical use. In this case, the pull mechanism can be controlled to retrieve the stent by manipulating the string or wire, but once the string or wire is withdrawn, retrieval of the stent is no longer possible. That is, in this case, the stent can be retrieved only once. However, the present invention is not limited to any particular type of drive component, and any drive component is applicable as long as it allows semi-retrieval of the stent.

The medical instrument of the present invention may further include a proximal fixation member, which is disposed at the first proximal end and configured to bring the stent into a closed configuration at the same end. The medical instrument may further include a distal fixation member and a pull mechanism. The pull mechanism may include a number of pull elements (including, but are not limited to, those capable of withstanding only tension, such as strings and wires, or those capable of withstanding both compression and tension). In the pull mechanism, each of the pull elements may be tied, at a first end, to the distal fixation member and, at a second end, to the first distal end. Additionally, the distal fixation member is configured to be able to move toward the proximal fixation member to cause the pull mechanism to switch the stent from the expanded configuration to the collapsed configuration around the first distal end, allowing semi-retrieval of the stent. The present invention is not limited to any particular shape of the protrusions on the stent's trailing section. For example, they may be serrated, wavy, trapezoidal or otherwise.

The inventors have found that, when the stent is compressed and collapses around the first distal end during delivery, tangling of the protrusions on the trailing section may occur, making the trailing section unable to expand after the stent is released. During the effort to overcome this problem, the inventors have also found that the tangling of the protrusions is basically attributable to winding and crossing of them that can be easily caused by their relative movement. Therefore, through effectively controlling relative movement of the protrusions by passing the clamping mechanism in the constraining structure through all or some of the protrusions, deformation of the stent during delivery can be effectively controlled to avoid tangling of its trailing section.

The medical instrument of the present invention may further comprise a delivery device for use with the stent. The delivery device may include a hollow push tube and a drive component. The hollow push tube may be detachably coupled at a distal end thereof to the first proximal end of the stent. The drive component may be inserted through the hollow push tube into the stent and detachably coupled within the stent to the first distal end thereof. In this way, the drive component can drive the stent to switch from the expanded configuration to the collapsed configuration around the first distal end. In preferred embodiments, the hollow push tube is detachably coupled at the distal end thereof to the aforementioned proximal fixation member, and the drive component is inserted sequentially through the hollow push tube and the proximal fixation member and detachably coupled to the distal fixation member. In this way, the drive component can drive the distal fixation member to move toward the proximal fixation member, which will in turn drive the pull mechanism to cause the stent to inwardly collapse around the first distal end thereof. Further, the body of the constraining structure may pass through the hollow push tube, the proximal fixation member and the distal fixation member and protrude out of the stent from the first distal end thereof, thereby allowing the clamping mechanism to unfold outside the first distal end to constrain the trailing section at the same end. Thus, the hollow push tube in the delivery device enables delivery, release and relocation of the stent, and the drive component in the delivery device enables loading and semi-retrieval of the stent. However, as previously described, as an alternative to the hollow pull tube, the drive component may be implemented as a flexible pull member.

The medical instrument of the present invention will be described in greater detail below with reference to the accompanying drawings. In the following description, its use for left atrial appendage (LAA) closure is described as an example, but this should not be construed as limiting the present invention in any sense.

Figure 2:
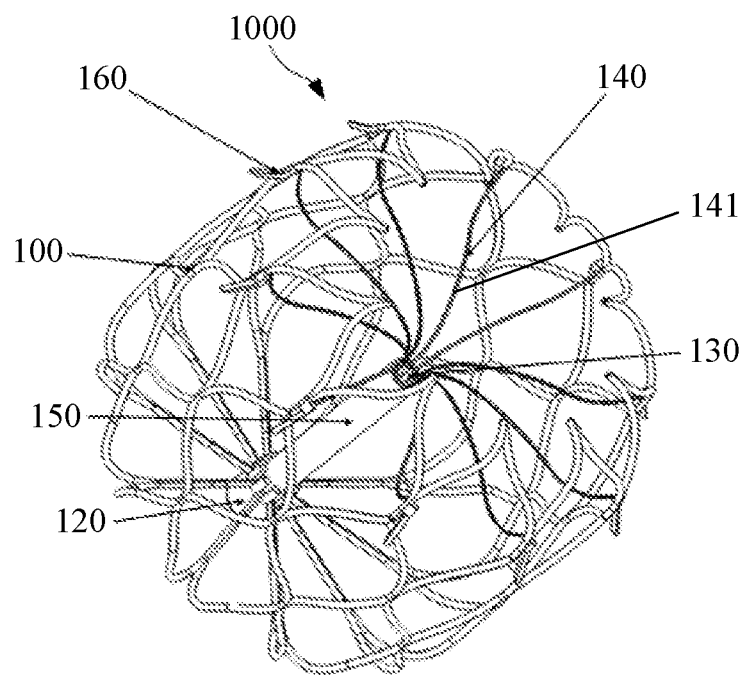
FIG. 2 is a schematic stereoscopic view of the structure of the medical instrument according to an embodiment of the present invention.
Figure 3:
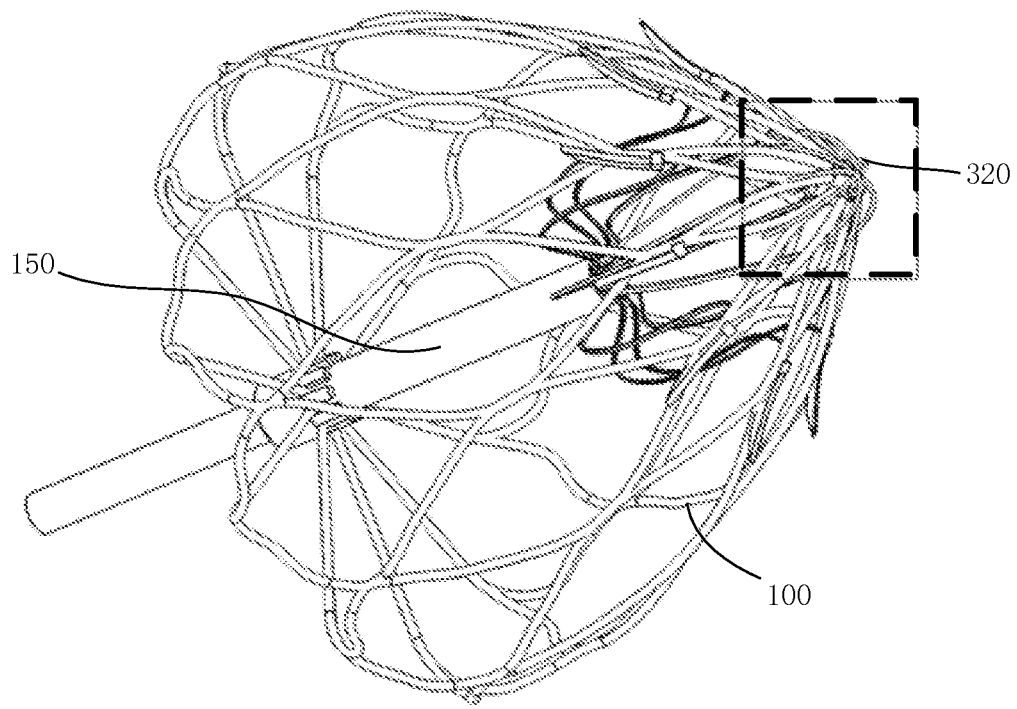
FIG. 3 shows the medical instrument in a configuration where a stent has been released while a trailing section thereof is not anchored yet, according to an embodiment of the present invention.

FIG. 1 is a schematic elevation view of the structure of a medical instrument according to an embodiment of the present invention. FIG. 2 is a schematic stereoscopic view of the structure of the medical instrument according to an embodiment of the present invention. FIG. 3 shows the medical instrument in a configuration where it has been released with a stent trailing section being unanchored according to an embodiment of the present invention. As shown in FIGS. 1 and 2, the medical instrument 1000 includes a stent 100, a delivery device 200 and a constraining structure 300.

Referring to FIG. 2, the stent 100 has a first proximal end and an opposing first distal end. The stent 100 is configured to be closed at the first proximal end and open at the first distal end. A trailing section at the first distal end includes a number of protrusions 111. The present invention is not limited to any particular shape of the protrusions 111, and non-limiting examples thereof include a serrated shape. The stent 100 further includes a proximal fixation member 120 disposed at the first proximal end to close the stent at this end. The stent 100 further includes a distal fixation member 130 and a pull mechanism 140. The pull mechanism 140 includes a number of pull elements 141. The present invention is not limited to any particular number of the pull elements 141, as long as the stent can be pulled at the first distal end and thus collapsed around this end. Specifically, the number of the pull elements 141 may be less than, equal to or greater than that of the protrusions 111. Preferably, the number of the pull elements 141 is equal to the number of the protrusions 111. Moreover, each of the pull elements 141 is connected, at a first end thereof, to the distal fixation member 130 and, at a second end thereof, to the first distal end.

Referring to FIG. 1, the delivery device 200 includes a hollow push tube 210 and a hollow pull tube 220. In practical use, a distal end of the hollow push tube 210 is detachably coupled to the first proximal end of the stent 100, more preferably to the proximal fixation member 120. The present invention is not particularly limited to how the coupling is established. Optionally, the distal end of the hollow push tube 210 may be threadedly coupled to the proximal fixation member 120. According to the present invention, the hollow pull tube 220 acts as drive component. It is inserted through the hollow push tube 210 and is detachably coupled within the stent 100 to the first distal end thereof. Preferably, the hollow pull tube 220 is inserted sequentially through the hollow push tube 210 and the proximal fixation member 120 and then detachably coupled to the distal fixation member 130. The present invention is not particularly limited to how the detachable coupling is established. Optionally, the hollow pull tube 220 may be threadedly coupled at a distal end thereof to the distal fixation member 130. Preferably, the stent 100 further includes a hollow guide member 150 proximally fixed to the first proximal end of the stent 100. Optionally, the hollow guide member 150 may be proximally fixed to the proximal fixation member 120 and arranged in coaxiality with the proximal fixation member 120 in order to allow the distal fixation member 130 and at least part of the pull mechanism 140 be inserted into the hollow guide member 150 from a distal end thereof. This facilitates control of the orientation and direction of the stent 100 when it is deformed for easier retrieval. Additionally, the hollow pull tube 220 is inserted through the proximal fixation member 120 into the hollow guide member 150 and detachably coupled to the distal fixation member 130. In this way, by pulling a proximal end of the hollow pull tube 220, the distal fixation member 130 will be driven to move toward the proximal fixation member 120 and then cause inward collapse of the stent 100 around the first distal end by acting on the pull mechanism 140. As a result of the collapse, all the protrusions 111 may come closer to, or even into abutment against, one another.

A body 310 of the constraining structure 300 is passed through the hollow push tube 210 and the stent 100 and then out of the stent 100 from the first distal end thereof. More specifically, the body 310 is sequentially passed through the hollow push tube 210, the proximal fixation member 120, the hollow guide member 150 and the distal fixation member 130 and then out of the stent 100 from the first distal end thereof so that a clamping mechanism 320 at a distal end of the body 310 is disposed outside the first distal end. The clamping mechanism 320 is configured for insertion into all or some of the protrusions 111 on the trailing section of the stent 100, which can limit relative movement of the protrusions 111 and constrain the stent's trailing section.

Specifically, the constraining structure 300 includes the body 310 and the clamping mechanism 320 disposed at the distal end of the body 310. In one embodiment, the clamping mechanism 320 includes plurality of, e.g., two, three, four, five or even more, clamping members 321. Referring to FIGS. 2 and 3, the clamping mechanism 320 includes a plurality of clamping members 321 inserted into some or all of the protrusions 111 to retain the trailing section of the stent that has been collapsed at the first distal end, preventing relative movement of all the protrusions 111 at the first distal end and thereby making them impossible to undesirably tangle with one another. In this way, the constraining structure and the hollow push tube when both loaded within the delivery sheath will not move relative to each other, facilitating shape control of the stent by an operator for easier delivery and retrieval. More specifically, in order to load the stent 100, the hollow pull tube 220 may be manipulated to slightly collapse the stent 100 around the first distal end thereof so that the stent 100 collapsed at the first distal end can be placed into the delivery sheath. Subsequently, the constraining structure 300 is passed into the stent 100 until the clamping mechanism 320 comes out of the stent 100 from the first distal end thereof, and the clamping mechanism 320 is then manipulated to engage and thereby firmly constrain the trailing section by virtue of its own structure, thus maintaining it in the collapsed configuration. At this point, the operator does not need to manipulate the hollow pull tube 220 anymore, allowing it to move relative to the hollow push tube 210 to mitigate deformation of the stent in the delivery sheath. In this way, for example, as shown in FIG. 3, the deformed stent's orientation and direction are well controlled. After the hollow push tube 210 is manipulated to push the stent 100 out of the delivery sheath, the constraining structure 300 may still constrain the stent's trailing section until the stent 100 is tuned to a desired target site. Following that, the body 310 of the constraining structure 300 may be pulled proximally so that the clamping mechanism 320 is expanded or deformed to no longer constrain the trailing section of the stent. Since this trailing section is elastic, it will self-expand by virtue of the resilience. As a result, anchoring features 112 on the stent are directed toward and then penetrate the LAA wall.

Figure 5A:
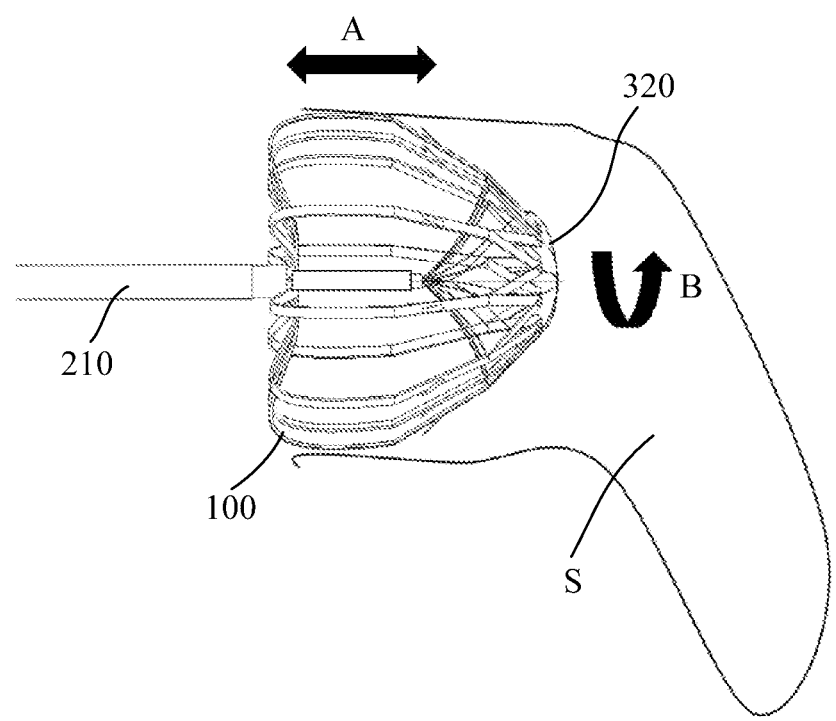
FIG. 5a schematically illustrates the medical instrument during its use for LAA closure in a configuration where the stent has been released while its trailing section is not anchored yet, according to an embodiment of the present invention.
Figure 5B:
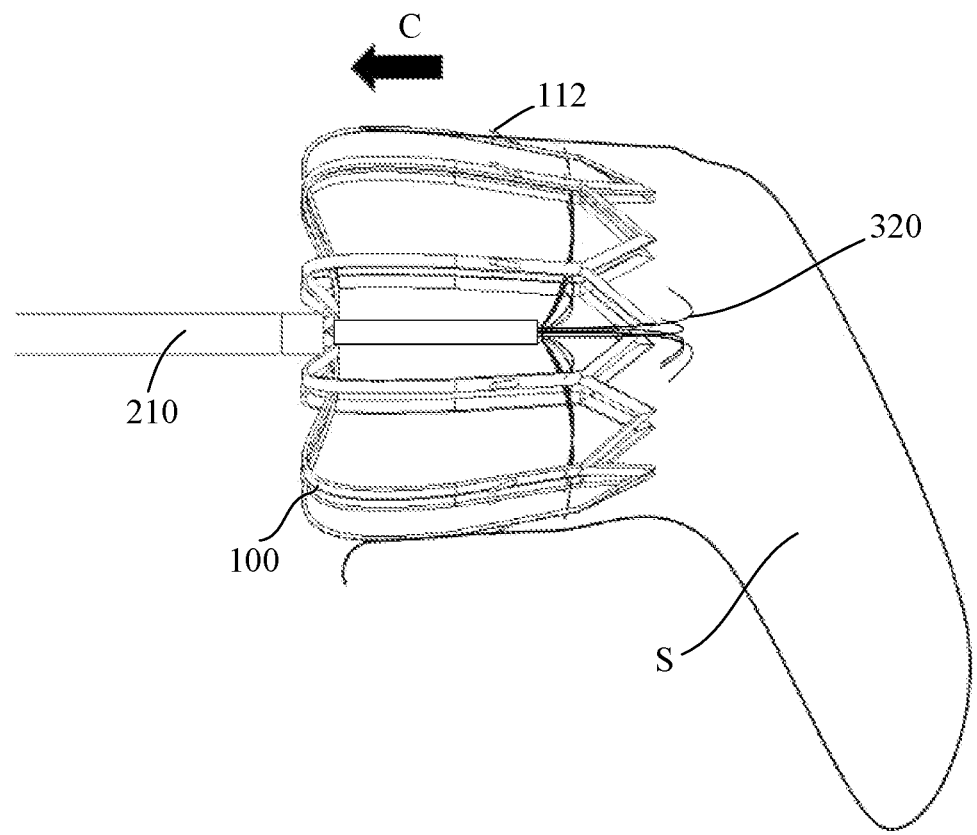
FIG. 5b schematically illustrates the medical instrument during its use for LAA closure in a configuration where the stent has been released within the LAA and the trailing section has expanded, according to an embodiment of the present invention.
Figure 5C:
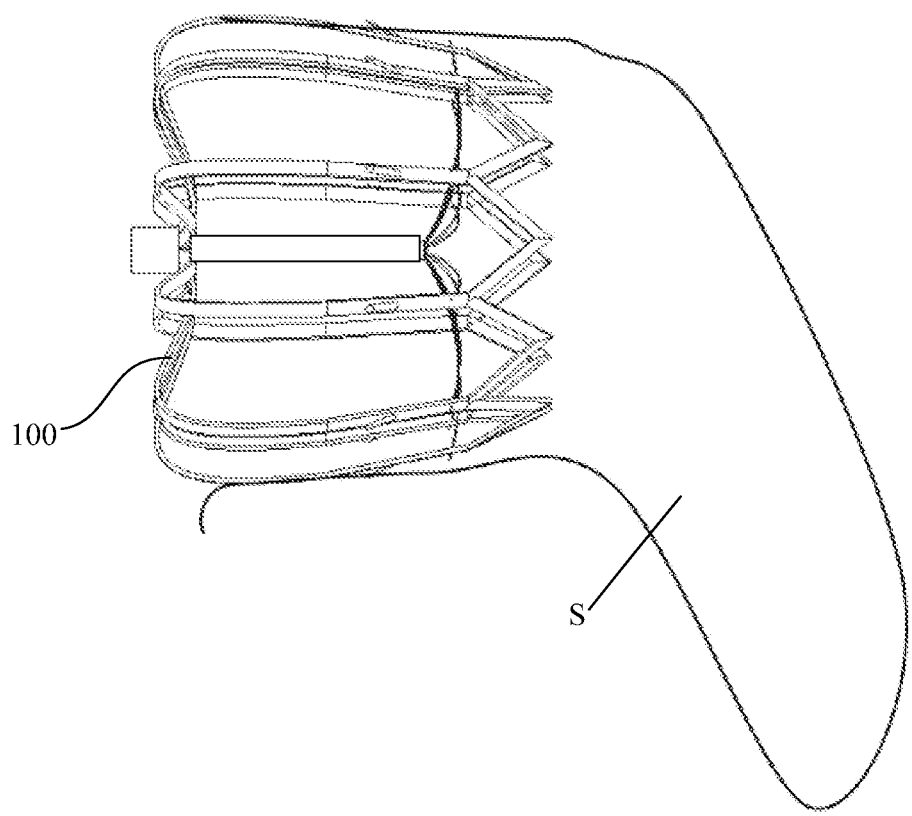
FIG. 5c schematically illustrates a configuration where a delivery device and a constraining structure have been withdrawn, with the stent remaining anchored in the LAA, according to an embodiment of the present invention.

A more detailed description is given below with reference to FIGS. 5a to 5c. At first, as shown in FIG. 5a, after the stent 100 is pushed out of the delivery sheath, it is introduced into the left atrial appendage (LAA) S while being constrained by the constraining structure 300. At this point, the hollow push tube 210 can be manipulated to adjust the position of the stent 100, for example, by moving it forth and back along the direction indicated by the arrow A, or by rotating it along the direction indicated by the arrow B, until it is positioned as desired. Next, as shown in FIG. 5b, after the stent 100 has been positioned as desired, the clamping mechanism 320 can be removed simply by pulling the constraining structure 300 gently by the operator. As a result, the trailing section of the stent 100 is freed, and the anchoring features 112 are enabled to penetrate the LAA wall. After that, the constraining structure 300 may be withdrawn along the direction indicated by the arrow C. Finally, as shown in FIG. 5c, after successful release of the stent 100, the operator may successively withdraw the constraining structure 300, the hollow push tube 210 and the hollow pull tube 220 from the human body, accomplishing the closure of the LAA.

Further, the clamping members 321 are preferably wire-like members with sufficient strength and desirable deformability, which enable firm clamping while allowing successful release by virtue of elastic deformation. Furthermore, the clamping members 321 may be made of an elastic material or a shape memory material, which imparts excellent deformability and sufficient mechanical properties to the clamping mechanism 320. For examples, the material of the clamping members 321 may be selected from a nickel-titanium alloy or stainless steel. More preferably, the clamping members 321 are nickel-titanium wires, optionally round nickel-titanium wires with a diameter optionally of 0.15 mm. Such nickel-titanium wires have sufficient stiffness and good deformability and allow a reduced size during delivery.

The present invention is not limited to any particular number of such clamping members 321, and the number may be determined depending on the size of the stent's trailing section. How the clamping members 321 retain the stent's trailing section will be described in greater detail below in the context of 10 protrusions 111 being provided on the trailing section of the stent 100, as an example.

Figure 4A:
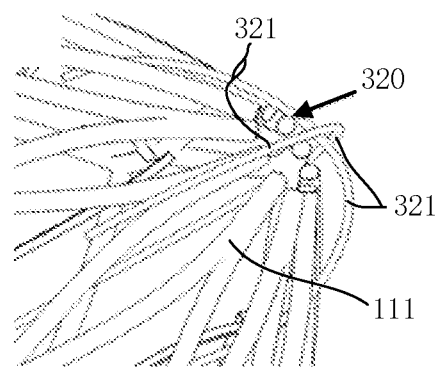
FIG. 4a is an enlarged partial view showing two clamping members made of two wires according to an embodiment of the present invention.
Figure 4B:
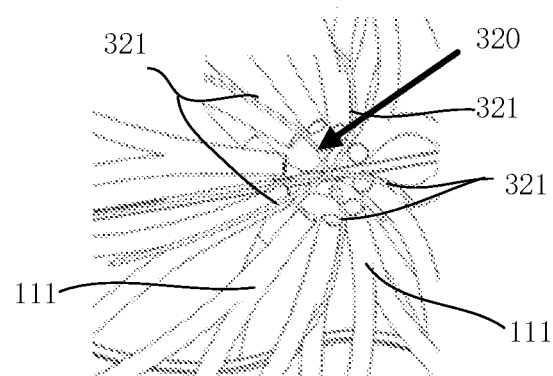
FIG. 4b is an enlarged partial view showing five clamping members made of five wires according to an embodiment of the present invention.
Figure 4C:
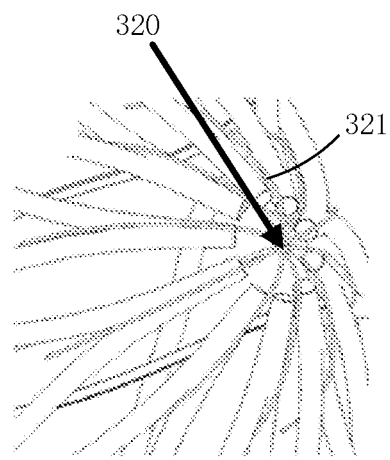
FIG. 4c is an enlarged partial view showing ten clamping members made of ten wires according to an embodiment of the present invention.

The structure of a portion encircled by the dashed box in FIG. 3 will be described with reference to its enlarged views. As shown in FIG. 4a, the clamping mechanism 320 may include two wires each having a shape resembling the letter "C" and crossing each other. The wires may provide two C-shaped clamping members 321 each defining two hooked fingers. The four hooked fingers may pass through and engage some of the protrusions 111. Moreover, because of interaction among the 10 protrusions on the stent, all these protrusions would be retained and prevented from relative movement. Alternatively, as shown in FIG. 4b, the clamping mechanism 320 may include five wires, each of which may be curved at one end to provide one clamping member 321. The five clamping members 321 formed by the wires may be spaced apart circumferentially and function like similar hooked fingers which may pass through and engage some of the protrusions 111. In this way, all the protrusions can also be effectively retained and prevented from relative movement. Yet alternatively, as shown in FIG. 4c, the clamping mechanism 320 may include ten wires. With similarity to the variant shown in FIG. 4b, each of the wires may be curved at one end to provide one clamping member 321, and the ten clamping members 321 may be spaced apart circumferentially and function like similar hooked fingers. However, in this case, all the protrusions 111 are populated and retained by the respective hooked fingers.

In other embodiments, each clamping member 321 may be shaped like the letter "V" and define two hooked fingers. In such embodiments, the clamping mechanism 320 may include only one clamping member 321 which is C-shaped or V-shaped, for example. Some of the protrusions 111 can be retained by passing the two hooked fingers of the clamping members 321 respectively into them. In alternative embodiments, the clamping mechanism 320 may include a plurality of clamping members 321. In these cases, the clamping members 321 may each define either one or two hooked fingers and may be used in combination. In the case of only one hooked finger, each clamping member 321 may be situated outside the stent 100 at one end and pass through one of the protrusions 111 at the other end. Moreover, the individual clamping members 321 may pass through different protrusions.

According to the present invention, limiting relative movement of all or some of the protrusions 111 by passing the clamping members 321 in the constraining structure 300 through the protrusions 111 can advantageously constrain the protrusions in a loose and orderly manner, which allows even easier expansion of the stent's trailing section. In the present embodiment, each protrusion 111 is a hollow structure defining an opening, through which one end of a clamping member 321 can pass to engage the stent 100.

It is added that in the case of the clamping mechanism 320 including a single clamping member, the clamping member may define two hooked fingers, and the number of the hooked fingers is smaller than the number of the protrusions. When the clamping mechanism 320 includes a plurality of clamping members 321, each clamping member 321 may define one hooked finger, and the number of the hooked fingers is smaller than or equal to that of the protrusions. That is, the number of the clamping members is smaller than or equal to the number of the protrusions.

A description is set forth below in the context of a plurality of clamping members 321. For example, the number of the clamping members 321 is equal to that of the protrusions 111 so that the protrusions 111 can be populated with the respective clamping members 321, as shown in FIG. 4c. As another example, the number of the clamping members 321 is less than the number of the protrusions 111. Preferably, the number of the protrusions 111 is twice that of the clamping members 321. For example, the former may be 10, and the latter may be accordingly 5. This can reduce the size of the clamping mechanism 320, allowing a smaller size during delivery. More preferably, the protrusions may be populated by the clamping members 321 so that there are one or more unpopulated protrusions between every two adjacent populated protrusions. Alternatively, in the case of 10 protrusions 111 and 5 clamping members 321, there may be one unpopulated clamping member 321 between every two adjacent populated protrusions. This can take into account both compactness during delivery and clamping performance. Further, more clamping members 321 with a smaller diameter may be provided. For example, when the number of the clamping members 321 is four or five, they may be made of round nickel-titanium wires with a diameter of 0.15 mm. As another example, when ten clamping members 321 are provided, they may be nickel-titanium wires with a diameter of 0.04 mm.

Figure 6:
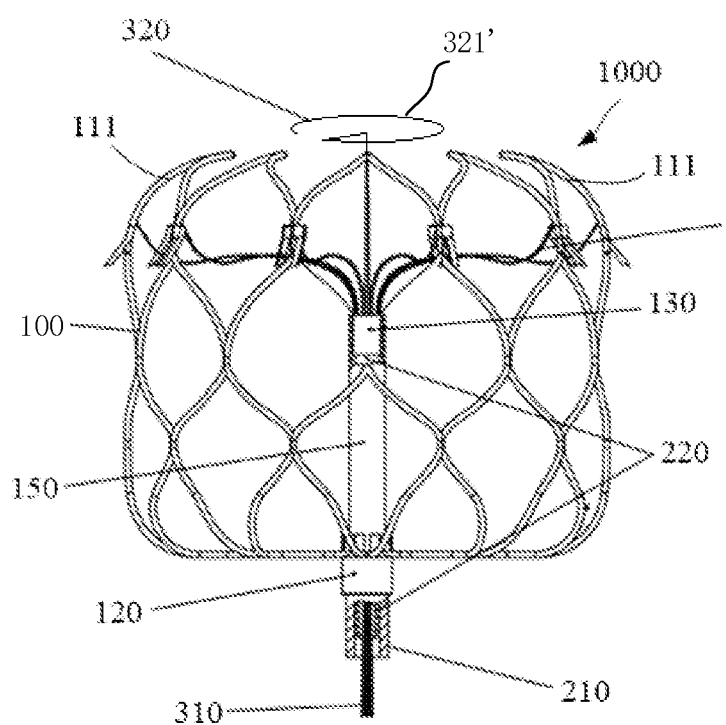
FIG. 6 is a schematic elevation view of the structure of a medical instrument according to another embodiment of the present invention.

FIG. 6 shows another embodiment of the constraining structure 300, in which a single clamping member 321' is included. The clamping member 321' may pass through either all or spaced ones of the protrusions. With 8 protrusions being provided as an example, the clamping members 321' may pass through the first, second, third, fifth, sixth and seventh protrusions clockwise, with the fourth and eight protrusions being unpopulated. Additionally, the clamping member 321' may be generally C-like or helical in shape. The C-like shape may have an opening. The present invention is not limited to any particular size of the opening, as long as all the protrusions can be effectively gathered and retained. The clamping members 321' is preferably an elastic wire such as a nickel-titanium wire or another nickel-based alloy wire. In operation, the clamping member 321' can be removed to release the stent's trailing section simply by gently pulling or turning the body 310. Therefore, it is convenient to operate. The present invention is not limited to any particular method of fabricating the constraining structure 300, and the fabrication can be accomplished in various ways. For example, the body 310 may be made as a straight rod, and the clamping mechanism 320 can be obtained by welding or otherwise attaching a number of wires (e.g., those as shown in FIGS. 4a to 4c) to a distal end of the straight rod. Alternatively, a number of wires may be each curved at one end and retained in a sleeve. For example, the sleeve may be configured as the body 310. Yet alternatively, the body 310 may be provided as a thick tube or wire, and a number of wires may be formed at its one end by cutting or otherwise. These wires may be then curved to form the clamping mechanism 320.

In the case of the clamping members 321 being curved relative to the body 310, each clamping member 321 may be curved relative to the body 310 at an angle preferably of 30°-180°, with 53°-72° being more preferred. The inventors have found from experiments that an angle of curvature of each clamping member 321 in that range can allow both effective retention and easy release. Here, if the direction from a proximal end of the body 310 to a distal end thereof is defined as a positive direction of an axis of the body 310, then the angle of curvature is defined as an angle of curvature of each clamping member 321 relative to the positive direction of the axis of the body 310.

Further, the stent 100 may further includes a biocompatible membrane covering part of an outer surface of the stent 100, with the protrusions being exposed therefrom.

It is to be noted that the present application also contemplates other structural variants of the clamping members. In addition, the stent may be either a braided stent or a cut stent, without limiting the present invention.

In summary, according to the techniques according to embodiments of the present invention, in practical use, the constraining structure of the present invention can desirably constrain the stent's trailing section so that the stent is deformed in a controlled manner and can be easily delivered within the delivery sheath while being able to easily expand upon it being pushed out thereof. Additionally, tangling of the stent's trailing section is prevented, ensuring a good success rate in release of the stent that has been pushed out of the sheath. Further, according to the present invention, after the stent is pushed out of the sheath, the anchoring features on the stent will not immediately anchor to the LAA wall. This can avoid damage to the patient's LAA wall caused by an operational error of the operator and reduce the risk of an accumulated pericardial effusion during surgery.

The foregoing description presents merely some preferred embodiments of the present invention and is not intended to limit the scope of the present invention in any sense. It is intended that all changes and modifications made by those of ordinary skill in the art in light of the above teachings fall within the scope of the appended claims.

What is claimed is:

1. A medical instrument, comprising a stent having a proximal end and an opposing distal end, wherein the distal end of the stent is configured with an expanded configuration and a collapsed configuration, wherein a trailing section of the stent at the distal end comprises a plurality of protrusions, and wherein the medical instrument further comprises a constraining structure comprising a body and a clamping mechanism, the clamping mechanism disposed at a distal end of the body, the body extending from the proximal end of the stent to the distal end thereof, the clamping mechanism limiting relative movement of the protrusions by passing through all or some of the protrusions, where the medical instrument further comprising a proximal fixation member, a distal fixation member and a pull mechanism, the proximal fixation member disposed at the proximal end of the stent and configured to bring the stent into a closed configuration at the proximal end, the pull mechanism comprising a number of pull elements each connected, at a first end, to the distal fixation member and, at a second end, to the distal end of the stent, the distal fixation member configured to be movable toward the proximal fixation member so that the distal end of the stent is allowed to switch from the expanded configuration to the collapsed configuration.

2. The medical instrument according to claim 1, wherein the clamping mechanism comprises a single clamping member which passes either sequentially through all the protrusions or spaced ones of the protrusions.

3. The medical instrument according to claim 1, wherein the clamping mechanism comprises at least one clamping member each passing at opposite ends through different ones of the protrusions.

4. The medical instrument according to claim 1, wherein the clamping mechanism comprises a plurality of clamping members arranged circumferentially around the stent, each of the clamping members passing at one end thereof through one of the protrusions, the clamping members passing through different ones of the protrusions.

5. The medical instrument according to claim 4, wherein a number of the clamping members is smaller than or equal to a number of the protrusions.

6. The medical instrument according to claim 5, wherein the number of the protrusions is twice the number of the clamping members.

7. The medical instrument according to claim 2, wherein the clamping member is a wire-like member made of an elastic material.

8. The medical instrument according to claim 7, wherein a material of the wire-like member is a nickel-titanium alloy or stainless steel.

9. The medical instrument according to claim 2, wherein the clamping member is shaped like the letter "C" or "V".

10. The medical instrument according to claim 3, wherein each of the clamping member(s) is curved relative to the body at an angle ranging from 30° to 180°.

11. The medical instrument according to claim 1, further comprising a biocompatible membrane covering part of a surface of the stent so that the protrusions are exposed therefrom.

12. The medical instrument according to claim 1, further comprising a delivery device comprising a hollow push tube and a drive component, the hollow push tube detachably connected at a distal end thereof to the proximal end of the stent, the drive component inserted through the hollow push tube into the stent and detachably connected within the stent to the distal end thereof, so as to cause the distal end of the stent to switch from the expanded configuration to the collapsed configuration, wherein the body extends from the proximal end of the stent through the hollow push tube to the distal end of the stent.

* * * * *